(12) United States Patent
Wako et al.

(10) Patent No.: US 10,285,886 B2
(45) Date of Patent: May 14, 2019

(54) LOAD MEASURING PIN SENSOR, WATCHING BED, AND WATCHING SYSTEM

(71) Applicants: SHINKO SHOJI CO., LTD., Tokyo (JP); PARAMOUNT BED CO., LTD., Tokyo (JP)

(72) Inventors: Taihei Wako, Yokohama (JP); Masanao Takizawa, Yokohama (JP); Toshiaki Yamazaki, Tokyo (JP); Yoshinori Ishibashi, Funabashi (JP); Hironobu Maezawa, Yokohama (JP)

(73) Assignees: SHINKO SHOJI CO., LTD., Tokyo (JP); PARAMOUNT BED CO., LTD., Tokyo (JP)

(*) Notice: Subject to any disclaimer, the term of this patent is extended or adjusted under 35 U.S.C. 154(b) by 0 days.

(21) Appl. No.: 15/900,131

(22) Filed: Feb. 20, 2018

(65) Prior Publication Data
US 2018/0235822 A1 Aug. 23, 2018

(30) Foreign Application Priority Data

Feb. 22, 2017 (JP) .................................. 2017-031596

(51) Int. Cl.
*A61B 5/00* (2006.01)
*A61G 7/05* (2006.01)
(Continued)

(52) U.S. Cl.
CPC .......... *A61G 7/0527* (2016.11); *A61B 5/1115* (2013.01); *G01L 1/2225* (2013.01);
(Continued)

(58) Field of Classification Search
CPC ...... G01G 19/52; G01G 19/445; G01G 23/36; G01G 3/13; A61B 5/1115; A61G 7/002;
(Continued)

(56) References Cited

U.S. PATENT DOCUMENTS 4,420,985 A * 12/1983 Raskin .................. G01L 1/2225
73/862.633
4,576,053 A * 3/1986 Hatamura ................. E02F 9/26
338/5

(Continued)

FOREIGN PATENT DOCUMENTS

CN 202382832 U 8/2012
CN 103353365 A 10/2013
(Continued)

OTHER PUBLICATIONS

Sep. 12, 2017 Notification of Reasons for Refusal issued in Japanese Patent Application No. 2017-031596.
(Continued)

*Primary Examiner* — Lisa M Caputo
*Assistant Examiner* — Brandi N Hopkins
(74) *Attorney, Agent, or Firm* — Oliff PLC

(57) ABSTRACT

A load measuring pin sensor disposed as a connecting pin in a connecting portion of a plurality of frames of a bed is provided. The load measuring pin sensor includes a shaft portion constituting the connecting pin, force point portions provided on the shaft portion where a load from one frame acts on the force point portions, a fulcrum portion provided at a position different from a position of the force point portions of the shaft portion where a stress from the other frame acts on the fulcrum portion, sensing portions provided at a portion connecting the force point portions, and the fulcrum portion of the shaft portion, and a strain gauge that detects strain occurring in the sensing portions.

7 Claims, 16 Drawing Sheets

(51) Int. Cl.
*G01L 1/22* (2006.01)
*A61B 5/11* (2006.01)
*A61B 5/08* (2006.01)
*A61B 5/024* (2006.01)

(52) U.S. Cl.
CPC ............. *A61B 5/0077* (2013.01); *A61B 5/024* (2013.01); *A61B 5/0816* (2013.01); *A61G 2203/20* (2013.01); *A61G 2203/32* (2013.01); *A61G 2203/36* (2013.01); *A61G 2203/44* (2013.01)

(58) Field of Classification Search
CPC .......... A61G 7/008; A61G 7/015; A61G 7/05; A61G 7/0507; A61G 7/05769; A61G 7/051; A61G 7/0527; A61G 2203/32; A61G 2203/74; A61G 7/0506; B60B 33/0021; B60B 33/0049; B60B 33/0068; B60B 33/021; G08B 5/36
See application file for complete search history.

(56) References Cited

U.S. PATENT DOCUMENTS

| | | | |
|---|---|---|---|
| 4,858,475 A * | 8/1989 | Jacobson | G01L 1/2225 73/862.631 |
| 5,419,210 A | 5/1995 | Haker | |
| 6,280,392 B1 | 8/2001 | Yoshimi et al. | |
| 2008/0214903 A1 | 9/2008 | Orbach | |
| 2014/0352060 A1* | 12/2014 | Hirose | A61G 7/05 5/310 |
| 2015/0300872 A1* | 10/2015 | Hirose | A61G 7/05 5/11 |

FOREIGN PATENT DOCUMENTS

| | | |
|---|---|---|
| JP | S57-040623 A | 3/1982 |
| JP | S57-129037 U | 8/1982 |
| JP | S60-083936 U | 6/1985 |
| JP | H02-280733 A | 11/1990 |
| JP | H04-070528 A | 3/1992 |
| JP | H10-038713 A | 2/1998 |
| JP | 3093745 B2 | 10/2000 |
| JP | 2001-070256 A | 3/2001 |
| JP | 3322632 B2 | 9/2002 |
| JP | 2006-346093 A | 12/2006 |
| JP | 2008-164495 A | 7/2008 |
| JP | 2008-532587 A | 8/2008 |
| JP | 2008-220603 A | 9/2008 |
| JP | 4514717 B2 | 7/2010 |
| JP | 4818162 B2 | 11/2011 |
| JP | 4857156 B2 | 1/2012 |
| JP | 2013-126432 A | 6/2013 |
| JP | 2016-123848 A | 7/2016 |
| WO | 2006/090371 A2 | 8/2006 |
| WO | 2013/108503 A1 | 7/2013 |
| WO | 2016/108266 A1 | 7/2016 |
| WO | 2016/208422 A1 | 12/2016 |

OTHER PUBLICATIONS

Nov. 5, 2018 Office Action issued Chinese Patent Application No. 201810154181.1.

* cited by examiner

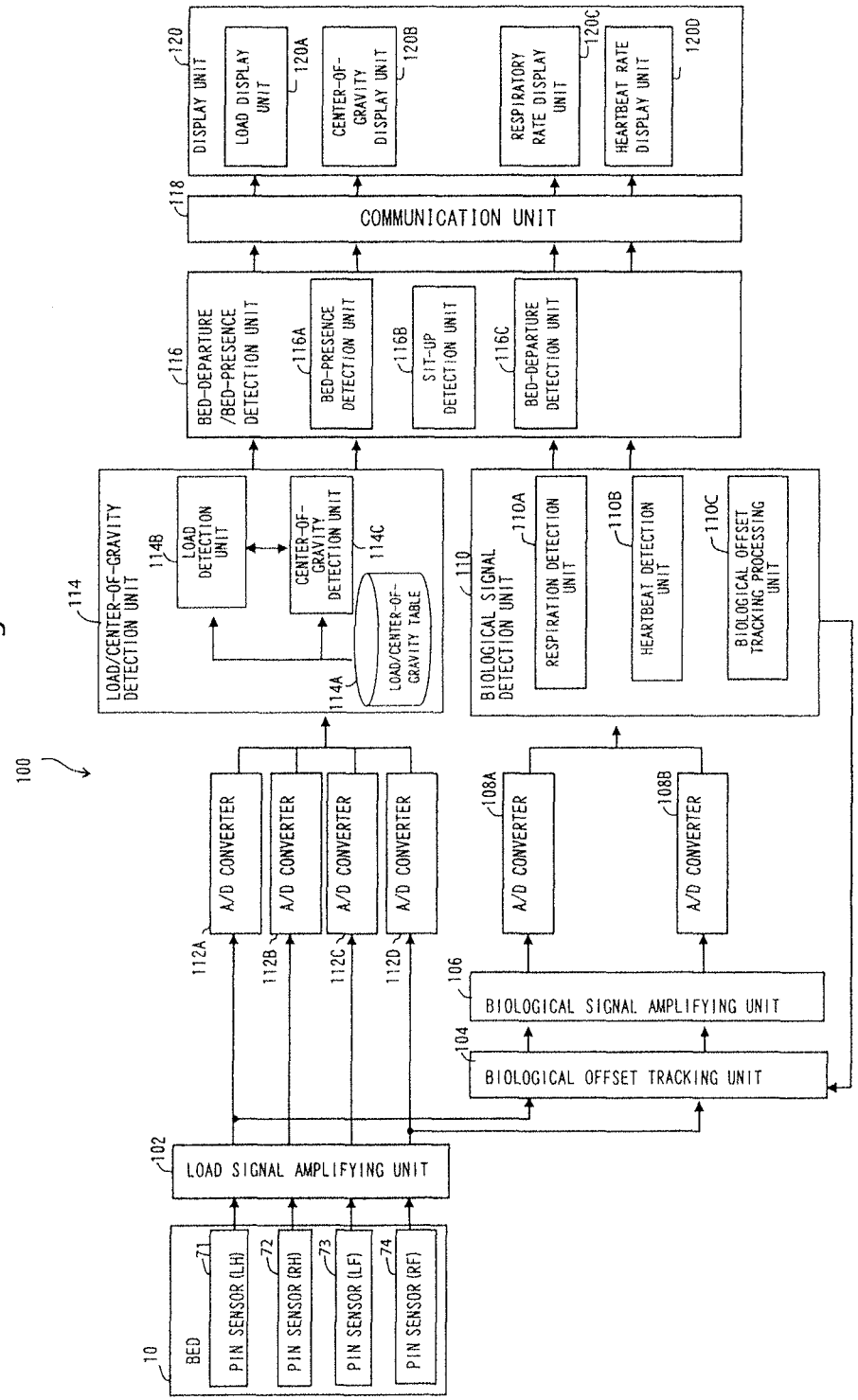

◇ POINTS WHERE LOAD RATIO OF RIGHT HEAD SENSOR 71 IS 10%

◆ POINTS WHERE LOAD RATIO OF LEFT HEAD SENSOR 72 IS 10%

LOAD MEASURING PIN SENSOR, WATCHING BED, AND WATCHING SYSTEM

TECHNICAL FIELD

The present invention relates to a load measuring pin sensor, a watching bed, and a watching system, and more particularly, in apparatuses for patient in a hospital or a nursing home such as a nursing bed, a bed for medical care, a motorized bed, and a nursing care lifter, or a bed for able-bodied people (hereinafter collectively referred to as bed), a load measuring pin sensor that is preferably used for measuring the load to obtain biological information such as weight, vibration, respiration, and heartbeat, can easily measure the load of a required portion of the bed, and can be easily installed on the bed in use in addition to at the time of bed manufacturing, a watching bed including the load measuring pin sensor, and a watching system including the watching bed.

BACKGROUND ART

In recent years, wandering of elderly people with dementia and accidents involving stumbling or falling around the bed have become a social problem, and countermeasures to these problems are required. In addition, it is expected that a quicker response in case of emergency can be made by monitoring the movement of users who are present on the bed for a long time, such as the elderly or the patient shortly after surgery, based on the load information of the bed.

For this purpose, for example, in Patent Literatures 1 to 3, a load detector is provided on a leg portion of a bed or between a leg portion and a floor to directly measure the load, or a torque sensor for indirectly measuring the load is provided in the elevating mechanism of the floor portion. Further, in Patent Literatures 4 and 5, a load detector is provided in a frame of a bed.

CITATION LIST

Patent Literature

Patent Literature 1: JP 02-280733 A
Patent Literature 2: JP 3093745 B2
Patent Literature 3: JP 3322632 B2
Patent Literature 4: JP 4818162 B2
Patent Literature 5: JP 4514717 B2
Patent Literature 6: JP 4857156 B2

SUMMARY OF INVENTION

Technical Problem

On the other hand, as described in Patent Literature 6, motorized beds are in practical use recently. However, conventionally, there was no load measuring sensor which is easily available for use in an existing bed.

The present invention has been made to solve the above-mentioned problems of the prior art, and its first object is to provide a load measuring pin sensor that does not rotate and which is easily available even for use in an existing bed.

A second object of the present invention is to provide a watching bed including the load measuring pin sensor.

A third object of the present invention is to provide a watching system including the watching bed.

Solution to Problem

The first object of the present invention is achieved by providing a load measuring pin sensor disposed as a connecting pin in a connecting portion of a plurality of frames of a bed. The load measuring pin sensor includes a shaft portion constituting the connecting pin, a force point portion provided on the shaft portion where a load from one frame acts on the force point portion, a fulcrum portion provided at a position different from a position of the force point portion of the shaft portion where a stress from the other frame acts on the fulcrum portion, a sensing portion provided at a portion connecting the force point portion and the fulcrum portion of the shaft portion, and a strain gauge that detects strain occurring in the sensing portion. One of the force point portion and the fulcrum portion has a cross section larger than a cross section of the shaft portion where the cross section of the one of the force point portion and the fulcrum portion has a shape other than a circular shape, and a pin sensor receiving portion on a frame side corresponding to the cross section of the one of the force point portion and the fulcrum portion is shaped to correspond to a shape other than the circular shape so that the load measuring pin sensor does not rotate. The other of the force point portion and the fulcrum portion has a portion of a spherical shape where the portion of the spherical shape is in contact with a frame.

The cross section of the one of the force point portion and the fulcrum portion can be a cross section of a fulcrum portion located at a longitudinal center of the shaft portion The shape other than the circular shape can be a quadrangle.

The sensing portion can have a prismatic shape having a rectangular cross section.

The strain gauge can be obliquely attached to the sensing portion.

The second object of the present invention is achieved by providing the watching bed including the load measuring pin sensor.

Here, the load measuring pin sensor can be provided at four frame connecting portions of the bed.

The third object of the present invention is achieved by providing the watching system including the watching bed including the load measuring pin sensor, a signal processing unit that processes an output of the load measuring pin sensor to obtain a biological signal, and a display unit that displays a processing result of the signal processing unit.

Here, the biological signal can include at least one of respiration and heartbeat.

Further, the signal processing unit may include a biological amplifier for amplifying a biological signal and a gain control circuit for dynamically controlling the gain of the biological amplifier in accordance with the amplitude of the biological signal to be measured.

Further, the signal processing unit can cancel the noise by adding the phase opposite to that of the output of the load measuring pin sensor disposed on the foot side of the bed to the output of the load measuring pin sensor disposed on the head side of the bed.

The watching system can include a monitor camera that monitors a measurement object on the bed

Effects of Invention

According to the present invention, a load can be measured by a pin sensor that is disposed as a connecting pin in a connecting portion of a plurality of frames of a bed, for example, in a connecting portion between upper and lower frames, wherein the pin sensor does not rotate, so that a pin sensor is easily available for use in an existing bed, and biological information on patient movement, respiration, and heartbeat can be easily acquired on the basis of the change in the load detected by the pin sensor.

Further, the watching bed having a load measuring function can be easily provided by the attachment of the pin sensor to the bed.

Further, the watching system which includes the watching bed can be easily provided.

BRIEF DESCRIPTION OF DRAWINGS

FIG. 7 is a block diagram showing the entire configuration of a first example of a watching system according to the first embodiment.

DESCRIPTION OF EMBODIMENT

Hereinafter, an embodiment of the present invention will be described with reference to the accompanying drawings. Note that the present invention is not limited by the description of the following embodiments and examples. Any component of the following embodiments and examples includes those easily thought of by the skilled person in the art and those significantly identical or what are called equivalents. In addition, components disclosed in the following embodiments and examples may be combined as appropriate or may be selected as appropriate.

Figure 1:
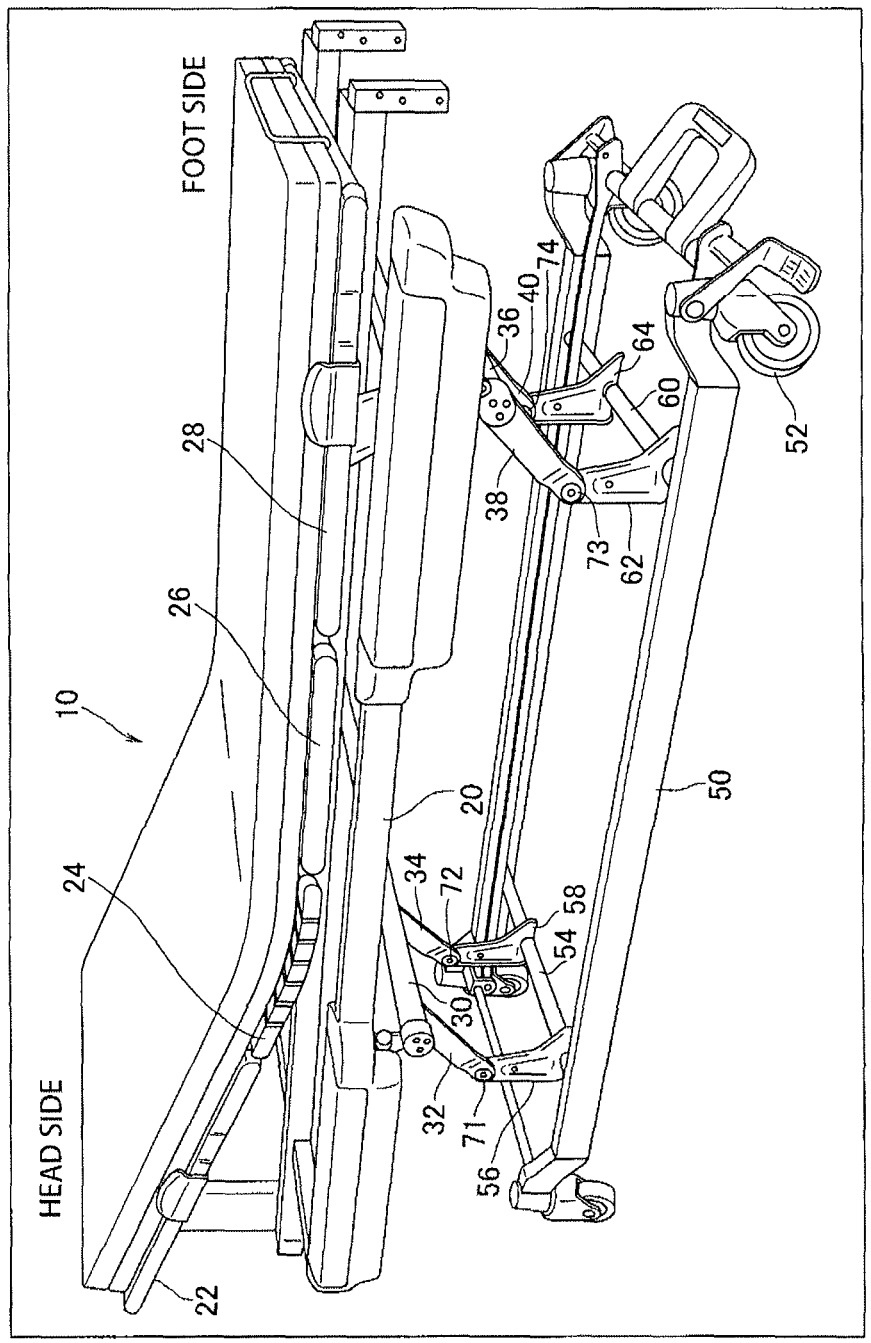
FIG. 1 is a perspective view of an example of the entire configuration of a motorized bed to which an embodiment of a pin sensor according to the present invention is attached when viewed from obliquely above.
Figure 2:
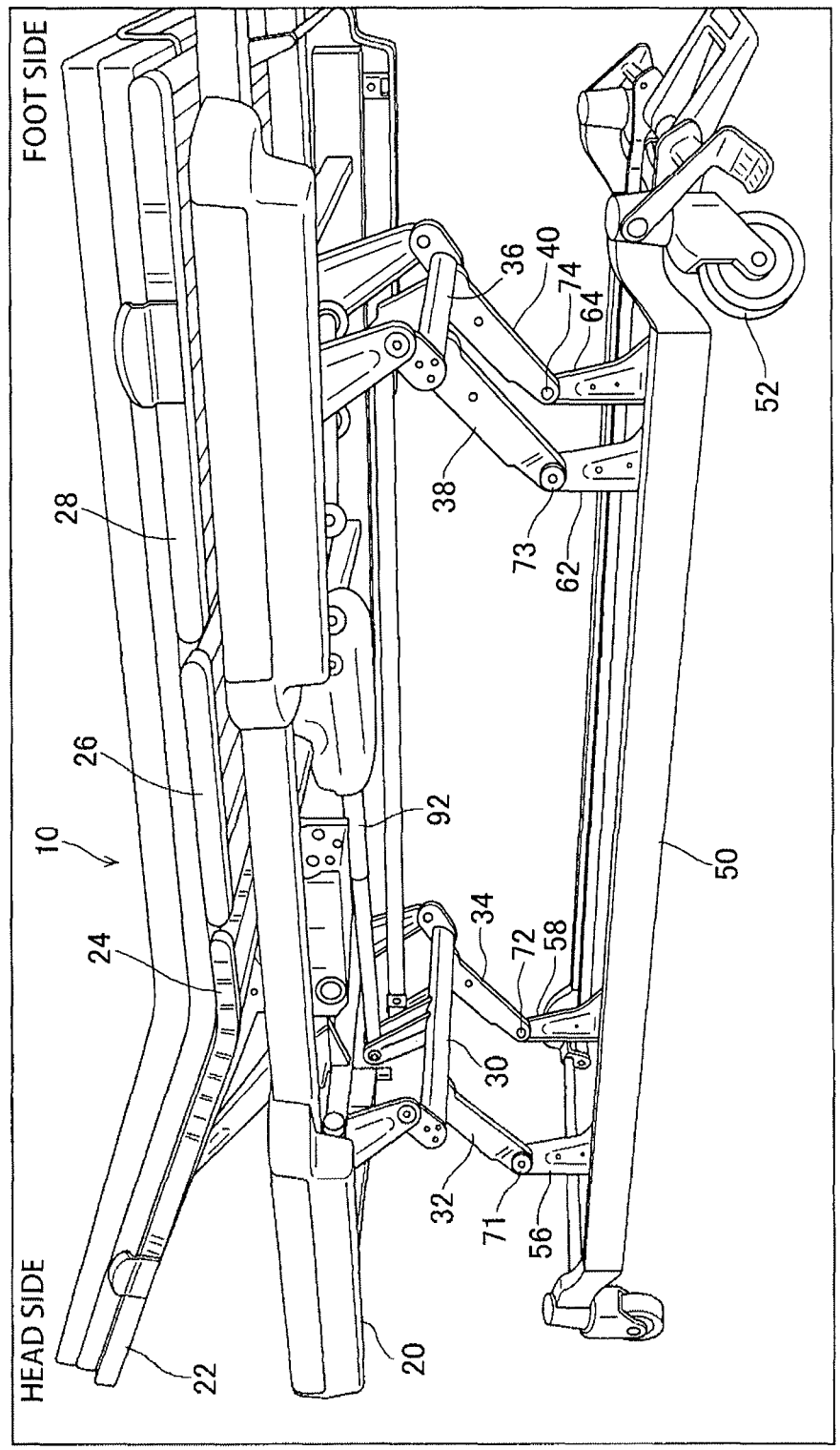
FIG. 2 is a perspective view of the example of the entire configuration of the motorized bed to which the embodiment of the pin sensor according to the present invention is attached when viewed from obliquely below.
Figure 3:
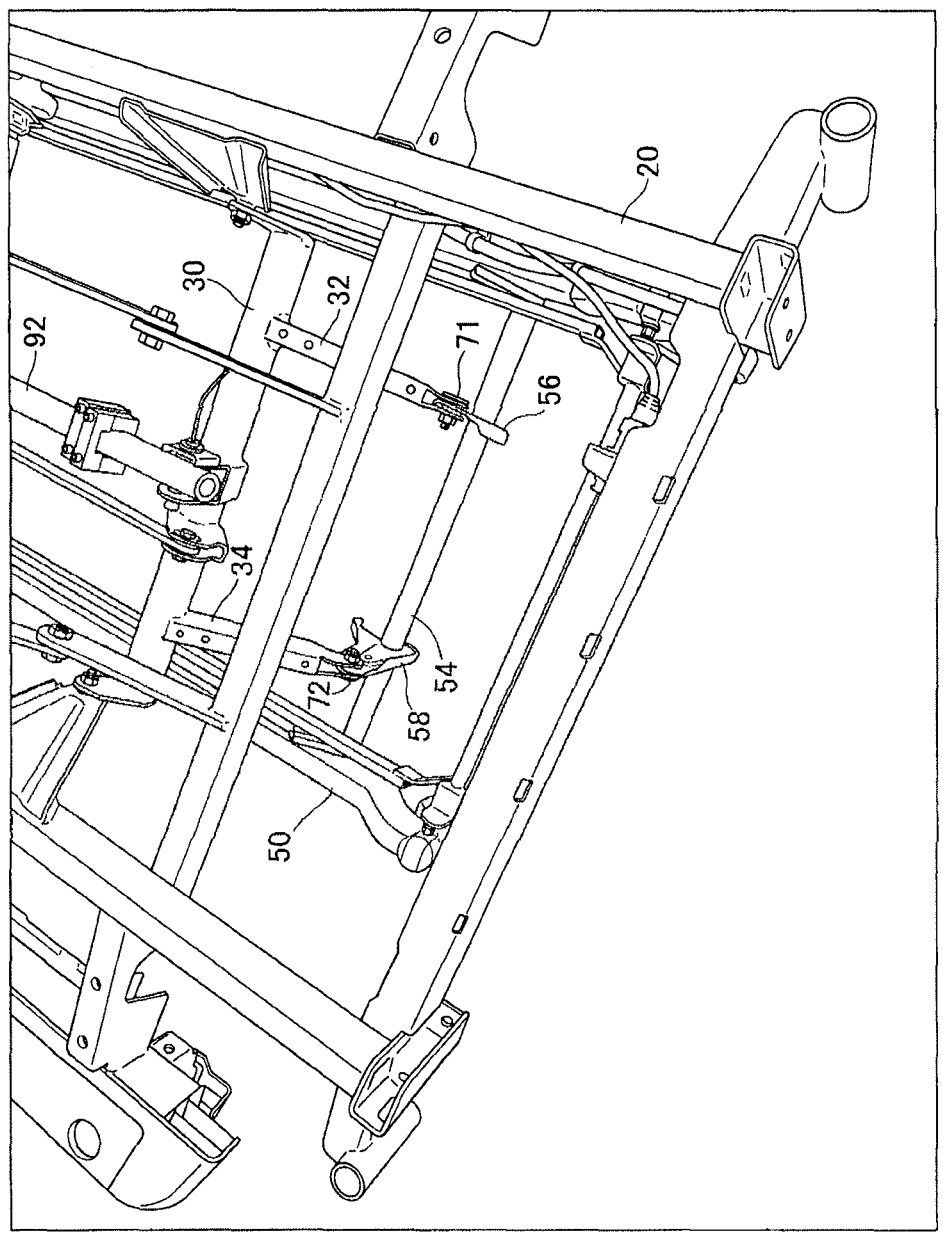
FIG. 3 is an enlarged perspective view of the head side of the motorized bed to which the embodiment of the pin sensor according to the present invention is attached when viewed from upper position.

As shown in FIGS. 1 to 3, a motorized bed 10 according to the embodiment of the present invention mainly includes an upper frame 20 capable of moving up and down and a lower frame 50 having moving wheels 52.

The upper frame 20 includes a back bottom 22, a waist bottom 24, a knee bottom 26, and a foot bottom 28 which are sequentially provided from the head side to the foot side of a patient.

Cylindrical pipes (referred to as lateral pipes) 30, 36, 54, and 60 are provided in the lateral direction on the head side and the foot side of the patient of the upper frame 20 and the lower frame 50.

With the motorized bed 10, the upper frame 20 supporting the back bottom 22 and the like moves up and down by the movement of a pipe (referred to as an outer pipe) 92 (refer to FIG. 2) constituting a rod of an actuator, so that the height of the upper frame 20 can be adjusted.

Below the back bottom 22, the waist bottom 24, the knee bottom 26, and the foot bottom 28, a back lifting device (not shown) for lifting the back bottom 22 and a knee lifting device (not shown) for raising the knee bottom 26 are provided.

Figure 4:
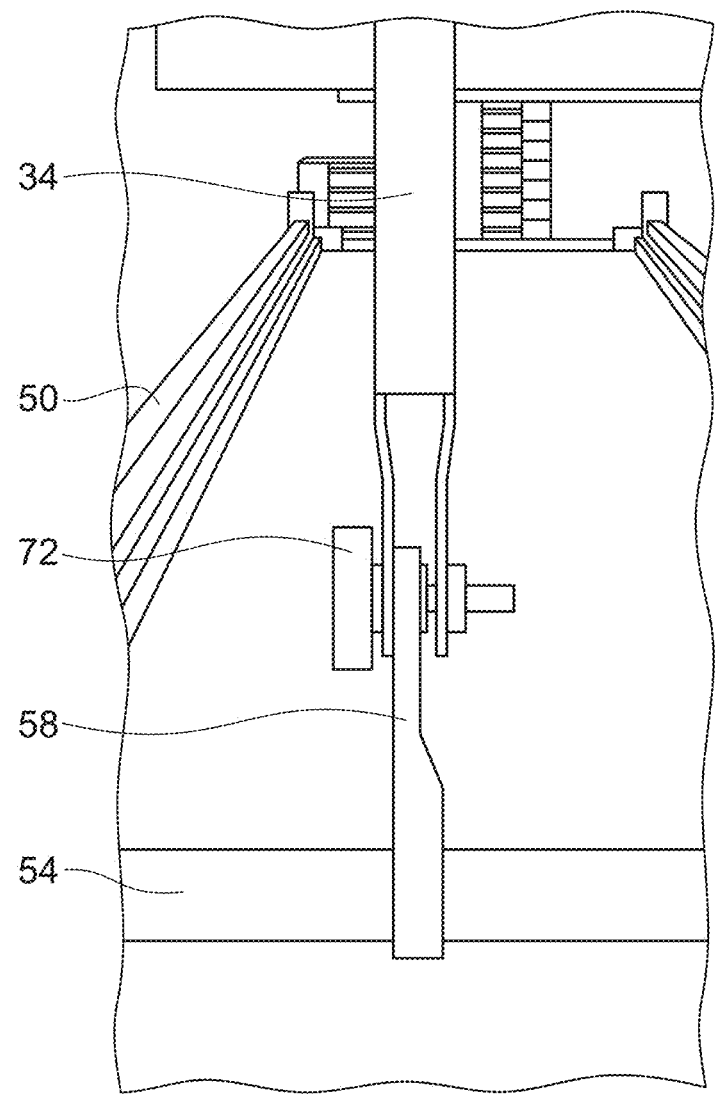
FIG. 4 is a photo, as an alternative to a drawing, showing a state in which the pin sensor according to the embodiment is attached.

The upper frame 20 includes a right stay 32 and a left stay 34 fixed to both sides of an upper frame head side lateral pipe 30, and a right stay 38 and a left stay 40 fixed to both sides of an upper frame foot side lateral pipe 36, and the lower frame 50 includes a right stay 56 and a left stay 58 fixed to both sides of a lower frame head side lateral pipe 54, and a right stay 62 and a left stay 64 fixed to both sides of a lower frame foot side lateral pipe 60. Corresponding stays 32 and 56, 34 and 58, 38 and 62, and 40 and 64 are connected to each other respectively by connecting pins 71, 72, 73, and 74 where the stays 34 and 58 are exemplified in FIG. 4.

Figure 5A:
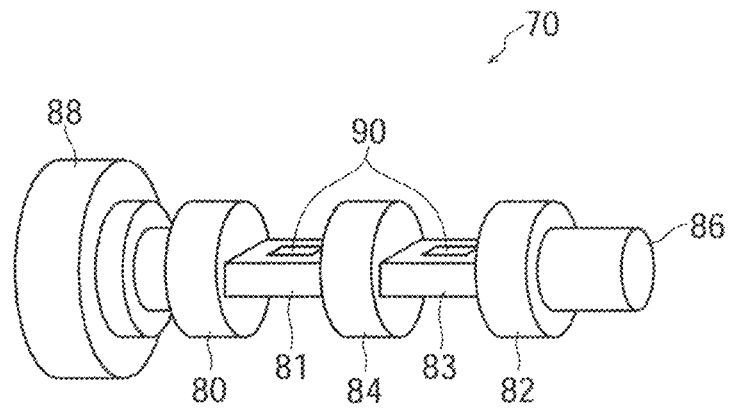
FIG. 5A is a perspective view of the configuration of the pin sensor.
Figure 5B:
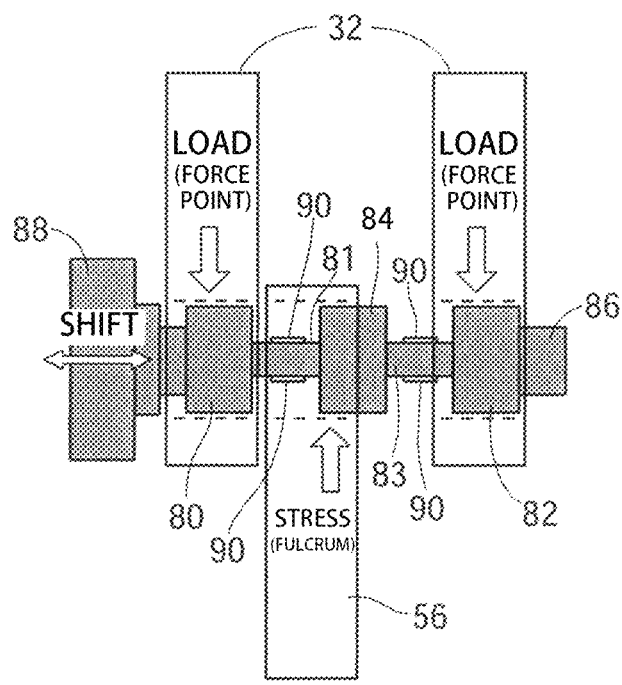
FIG. 5B is a cross sectional view showing the state in which the pin sensor is mounted according to a reference embodiment.

In the reference embodiment, a pin sensor 70 as shown in FIGS. 5A and 5B is used as the connecting pins 71 to 74.

The reference embodiment of the pin sensor 70 exemplifying the case of the connecting pin 71 in FIGS. 5A and 5B includes two force point portions 80 and 82 on which the load of the upper frame 20 acts via, for example, the stay 32, a fulcrum portion 84 on which the stress of the lower frame 50 acts via, for example, the stay 56, sensing portions 81 and 83 connecting the force point portions 80 and 82 to the fulcrum portion 84, a shaft portion 86, a head portion 88, and a strain gauge 90 for converting to an electric signal the distortion occurring in the sensing portion 81 between the force point portion 80 and the fulcrum portion 84 and the sensing portion 83 between the fulcrum portion 84 and the force point portion 82.

The force point portions 80 and 82, and the fulcrum portion 84 have a cylindrical shape.

The sensing portions 81 and 83 are long in the horizontal direction and have a horizontally elongated prismatic shape having necessary thickness in the up and down direction, and is configured to secure the strength as a connecting pin.

In the reference embodiment, the shape of the pin is similar to a pin of the existing bed so that it can be replaced with the existing pin.

In addition, the shape is such that a portion subjected to a load and a portion to be strained are clearly distinguished.

The strain gauge 90 is attached to the upper and lower surfaces of the sensing portions 81 and 83, for example, by a bending method, and a total of four sheets of strain gauges 90 are provided on the upper and lower sides of the sensing portions that sandwich the fulcrum portion 84. Connecting the gages in a bridge shape allows its output to be detected with high sensitivity. Here, the number of sheets of strain gauges can be one, two, or four. The accuracy increases as the number of sheets of strain gauges increases. In the reference embodiment, the number of sheets of strain gauges is four, and a bridge circuit is constituted by four sheets of strain gauges.

Figure 6A:
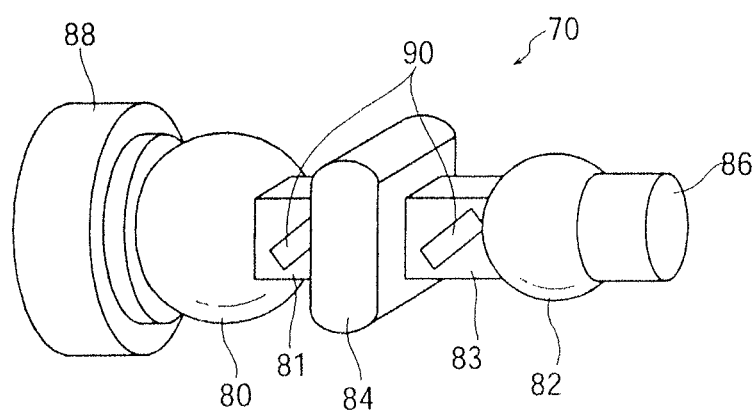
FIG. 6A is a perspective view of the configuration of the pin sensor.
Figure 6B:
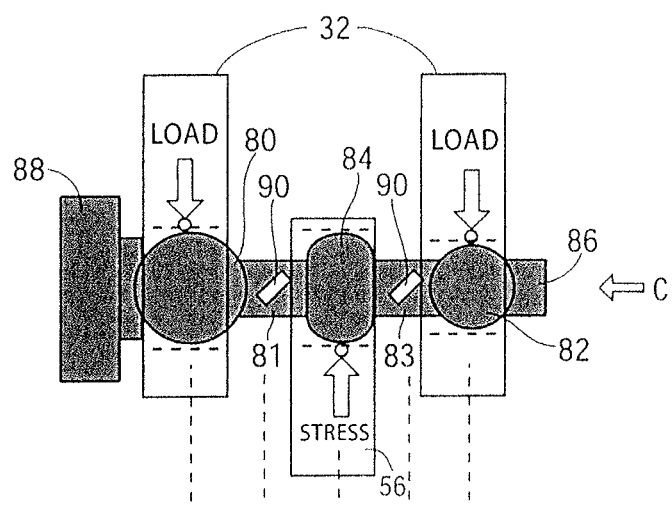
FIG. 6B is a sectional view showing the state in which the pin sensor is mounted.

FIG. 6A shows the pin sensor 70 according to a first embodiment of the present invention. In the present embodiment, the force point portions 80 and 82, and the fulcrum portion 84 of the reference embodiment have a portion that contacts the frame (in this case, the stays 32, 56) wherein the portion has a spherical shape, and the configuration is such that force is received by a point. Thus, as shown in FIG. 6B, even if the stay (32) is shifted in the axial direction, the position where the stay (32) comes into contact with the force point portion (80, 82) is almost unchanged. In addition, even if the stay (56) is shifted in the axial direction, the position where the stay (56) contacts the fulcrum portion (84) is almost unchanged. Therefore, the shift of the pin sensor 70 and the frame (32, 56) does not affect the fulcrum point or the force point, and the variation of the load value due to the axial shift becomes small.

Figure 6C:
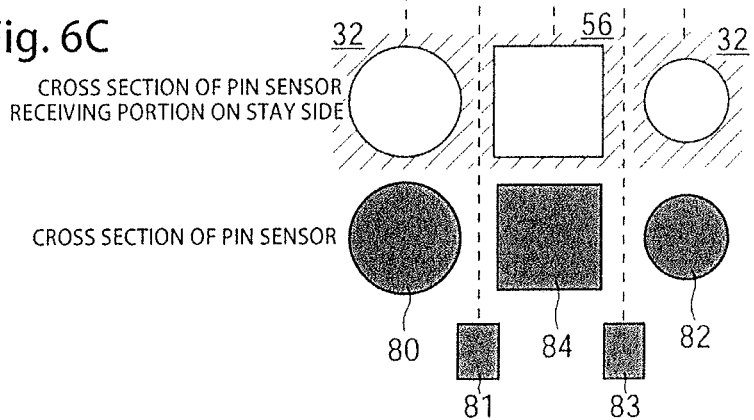
FIG. 6C is a cross sectional view showing cross sections of the pin sensor and a pin sensor receiving portion on the stay side according to a first embodiment of the present invention.

Furthermore, in this first embodiment, as shown in FIG. 6C (cross sectional view seen from the direction of arrow C in FIG. 6B), the cross section of the fulcrum portion 84, which is, for example, disposed at the center of the pin sensor 70, is formed into a quadrangular shape, and the cross section of the pin sensor receiving portion on the frame side (the stay 56) corresponding to the cross section of the fulcrum portion 84 is formed into a corresponding quadrangular shape so that the pin sensor 70 does not rotate.

The sensing portions 81 and 83 according to the first embodiment are long in the up and down direction and have a vertically elongated prismatic shape having necessary thickness in the horizontal direction, and is configured to secure the strength as a connecting pin.

The strain gauge 90 of the present embodiment is of a shearing type, and the outputs of a total of four sheets of strain gauges 90 which are symmetrically attached to opposite sides of the sensing portions 81 and 83 on the forward and rear side at an oblique angle of 45° are connected in a bridge shape, so that it is possible to detect with high sensitivity the shear strain generated from the load applied to the fulcrum portion 84 and the force point portions 80 and 82. Here, the number of sheets of strain gauges can be one, two, or four. The accuracy increases as the number of sheets of strain gauges increases. In the present embodiment, the number of sheets of strain gauges is four, and a bridge circuit is constituted by four sheets of strain gauges.

It is also possible to suppress the rotation of the pin sensor 70 of the reference embodiment by adding a configuration similar to that of the fulcrum portion 84 of the first embodiment to the fulcrum portion 84 and the force point portions 80 and 82 of the reference embodiment.

Note that the reference embodiment may employ a shearing type, and the first embodiment may employ a bending type.

In this way, it is possible to detect the load applied to the connecting portion of the upper and lower frames of the bed housing. By detecting the vibration (wave) transmitted to the housing of the motorized bed 10 from the load applied to the portion and the change in the load, it is possible to detect biological information including respiration and heartbeat. Therefore, it is possible to detect the respiration and heartbeat of a sleeping person in a non-contact manner by merely putting a person to the motorized bed 10.

The position at which the pin sensor 70 is used is not limited to the positions of the connecting pins 71 to 74, and may be different four points which receive the total load of the bed. Depending on the structure of the bed, the number is not limited to 4 points.

FIG. 7 is a block diagram showing the entire configuration of a first example of a watching system which employs the pin sensor according to the first embodiment.

Figure 8:
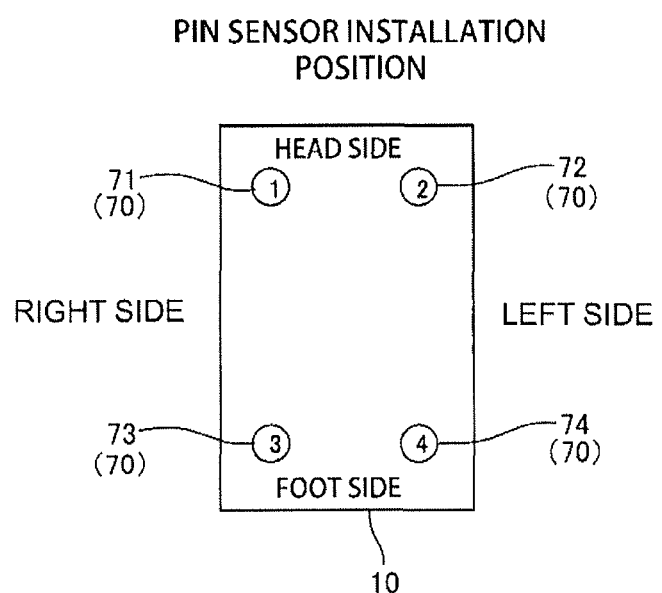
FIG. 8 is a plan view showing the arrangement position of a pin sensor used as a connecting pin to a bed with respect to the watching system according to the first embodiment.

In the first example, as shown in FIG. 8, the pin sensors 71 to 74 are disposed on the left and right sides of the head side and on the left and right sides of the foot side of the motorized bed 10.

Here, in order to obtain biological information such as respiration and heartbeat, by using at least diagonally positioned two sensors such as pin sensors 71 and 74, or 72 and 73, it is possible to detect a biological signal in the whole bed.

Further, in order to obtain the load/center-of-gravity information, by using all pin sensors 71 to 74, the load and the center-of-gravity can be detected with high accuracy.

As shown in FIG. 7, the outputs of the pin sensors 71 to 74 are input to a load signal amplifying unit 102 of a signal processing unit 100. Among the outputs of the pin sensors amplified by the load signal amplifying unit 102, for example, the outputs of the pin sensors 71 and 74 are input to a biological offset tracking unit 104. The output of the biological offset tracking unit 104 is input to a biological signal amplifying unit 106. The output of the biological signal amplifying unit 106 is converted into a digital signal by biological A/D converters 108A and 108B, and thereafter is input to a biological signal detection unit 110 including a respiration detection unit 110A, a heartbeat detection unit 110B, and a biological offset tracking processing unit 110C.

Figure 9:
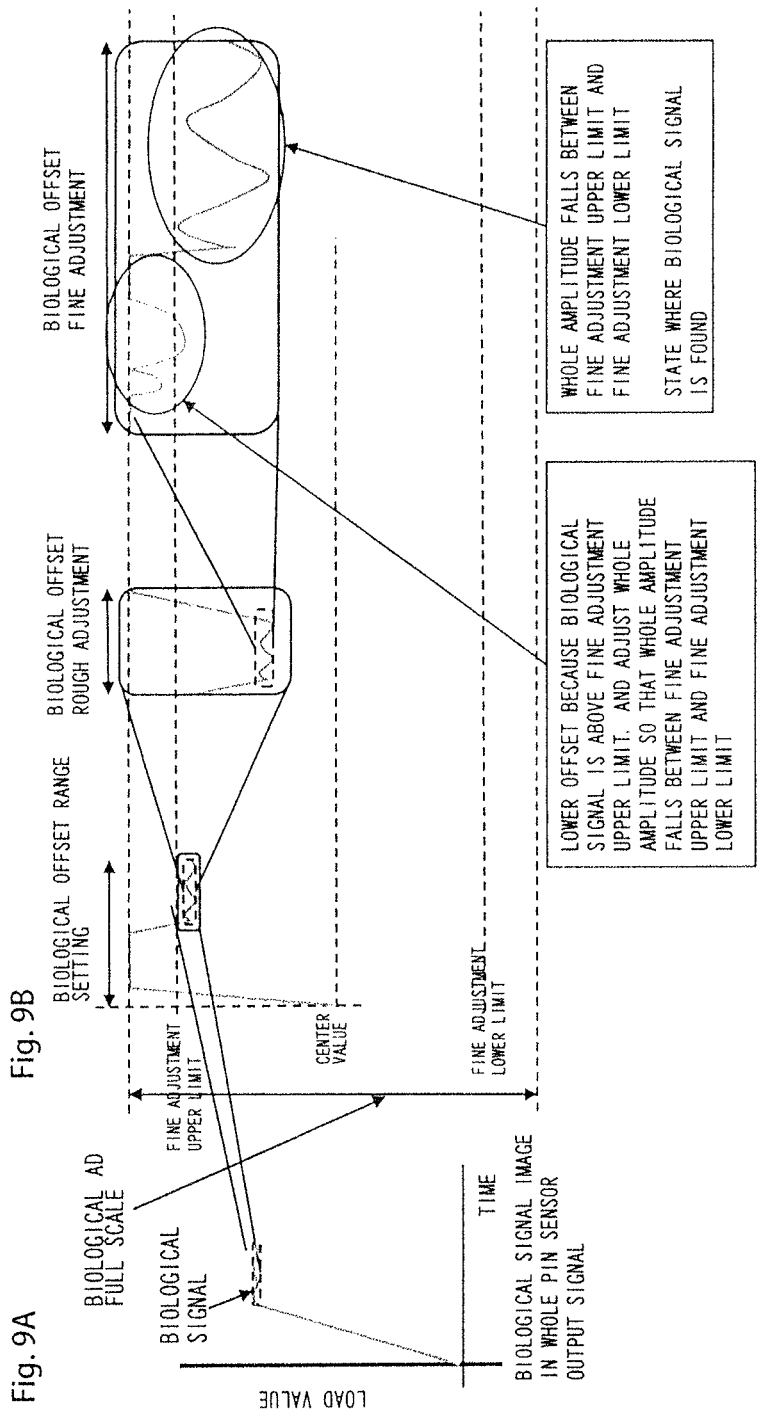
FIG. 9A is a diagram showing an example of a biological signal and FIG. 9B is of a change in the signal during processing with respect to the watching system according to the first embodiment.

The range of change in the biological signal with respect to the range of change in the entire load value of the pin sensor output signal is very small as illustrated in FIG. 9A. Therefore, in the biological offset tracking processing unit 110C, tracking processing as shown in FIG. 9B and FIG. 10 is performed to find a biological signal.

Figure 10:
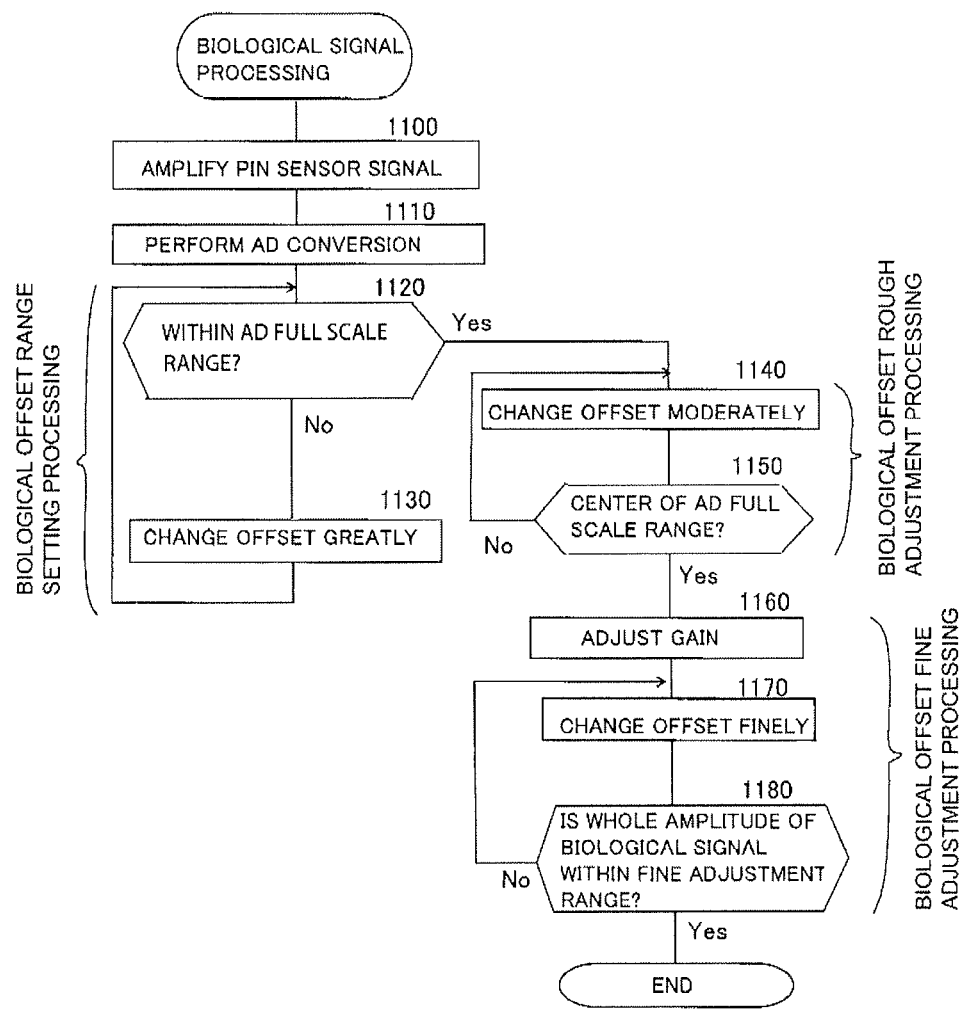
FIG. 10 is a flow chart showing processing procedure of the biological signal with respect to the watching system according to the first embodiment.

Specifically, in step 1100 in FIG. 10, the output signals of the pin sensors 71 and 74 are amplified by the load signal amplifying unit 102 and the biological signal amplifying unit 106.

Next, in step 1110, the amplified signal is input to the biological A/D converters 108A and 108B to acquire a biological AD value. A waveform constituted by the acquired signals arranged in time series is a biological signal.

First, a biological offset range setting process is performed on the biological signal.

Specifically, the process proceeds to step 1120, in which it is determined whether the biological signal is in the biological AD full scale.

When the determination result is "No", the process proceeds to step 1130 where the biological offset is largely changed, and the biological AD value is adjusted so as to be a state closest to the center of the range of the biological AD full scale.

When the determination result of step 1120 is "Yes", the process proceeds to step 1140 where the biological offset rough adjustment processing is performed.

Specifically, in step 1140, the biological offset is moderately and finely changed in comparison with the biological offset range processing, and adjusted so that the biological AD value is a value close to the center of the range of the biological AD full scale range.

When the result of step 1150 is "Yes", the biological offset fine adjustment processing is performed.

Specifically, in step 1160, the gain for the biological signal is set for a fine adjustment, and the signal is amplified. In step 1170, the offset of the biological signal is finely adjusted, and the whole amplitude of the biological signal is adjusted so as to fall within the fine adjustment range between the fine adjustment upper limit and the fine adjustment lower limit.

When it is determined in step 1180 that the entire amplitude of the biological signal falls within the fine adjustment range between the fine adjustment upper limit and the fine adjustment lower limit, the process of finding the biological signal ends.

On the other hand, the output signals of the four pin sensors 71 to 74 are amplified by the load signal amplifying unit 102 and then input to load A/D converters 112A, 112B, 112C and 112D, respectively, and subjected to A/D conversion to acquire the load AD value.

Detection of the load value on the bed is carried out in the following procedure.

No. 1 First, the load AD value immediately after power-on and immediately after reset is set to "0" offset value.

No. 2 Next, the value obtained by subtracting "0" offset value from the load AD value when load is applied to the bed is multiplied by the sensitivity correction coefficient for correcting the difference in sensitivity for each pin sensor. This multiplied value is the load value for each pin sensor.

No. 3 Next, by summing the load values for each pin sensor, the load value on the bed can be detected.

In this manner, the load value obtained in real time on the bed is input to a load/center-of-gravity detection unit 114 including a load/center-of-gravity table 114A, a load detection unit 114B, and a center-of-gravity detection unit 114C.

At this time, the phase opposite to that of the output signals of the pin side sensors 73 and 74 on the foot side is added to the output signals of the pin sensors 71 and 72 on the head side to cancel external noise due to vibration of floor and air superimposed on an electric signal, so that it is possible to improve the biological detection accuracy. Since there is the vibration of the living body also in the pin sensors 73 and 74 on the foot side, the biological signal also attenuates. However, the S/N ratio improves because the attenuation effect of the external noise due to the floor and air vibration is high.

Figure 11:
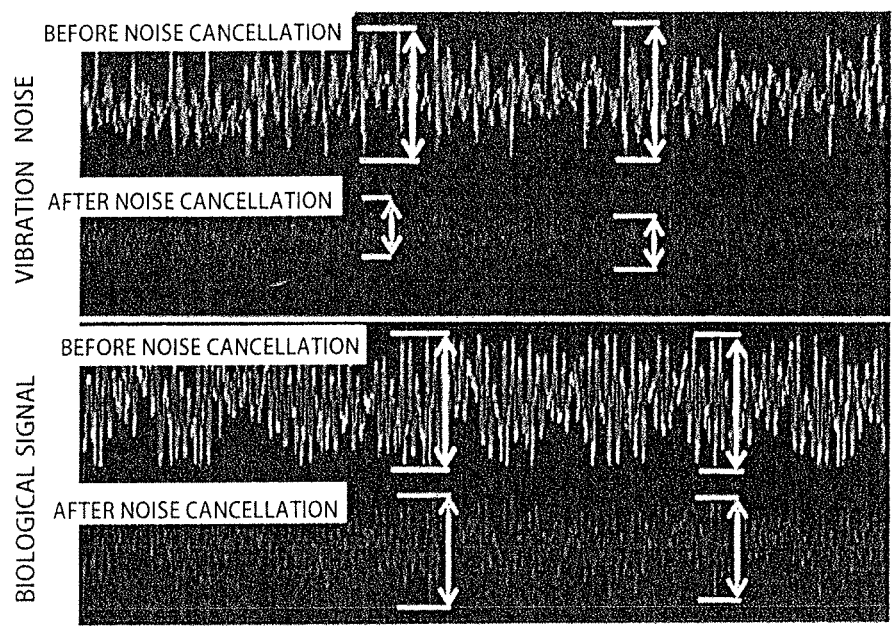
FIG. 11 is a diagram showing an example in which noise is canceled with respect to the watching system according to the first embodiment.

In the example, as shown in FIG. 11, it was determined that while the vibration noise is reduced by about 50%, the biological signal is reduced by about 30%, and the S/N ratio is improved by 1.4 times or more.

The detection of the center-of-gravity position on the bed by the load detection unit 114B can be performed, for example, as follows.

Here, the center-of-gravity position is detected based on the ratio of the load value for each of the four pin sensors using the load value on the bed for each pin sensor which has been previously obtained.

1) First, based on the load value on the bed for each pin sensor, and the load table as shown in Table 1, the center-of-gravity position between the two points is detected for each combination of the following two points among the four pin sensors 71 to 74.

Two points at a right head sensor 71 and a left head sensor 72

Two points at the right head sensor 71 and a right foot sensor 73

Two points at the left head sensor 72 and a left foot sensor 74

Two points at the right foot sensor 73 and the left foot sensor 74

For example, in a case where calculating the center-of-gravity position from two points at the right head sensor 71 and the left head sensor 72, the following procedure is used.

First, the ratios of the right head load and the left head load to the total of the four loads are calculated. A load table as shown in Table 1 is used to calculate the load ratio.

TABLE 1

| Up and down position | Left and right position | Right head load ratio | Left head load ratio | Right foot load ratio | Left foot load ratio |
|---|---|---|---|---|---|
| Head side | Right side (Sample point 1) | 67% | 21% | 30% | −17% |
|  | Center | 16% | 79% | 5% | 0% |
|  | Left side (Sample point 2) | −19% | 117% | −13% | 15% |
| Head side center | Right side | 54% | 6% | 48% | −8% |
|  | center | 11% | 58% | 19% | 12% |
|  | Left side | −19% | 90% | 0% | 28% |
| Center | Right side | 25% | −2% | 70% | 7% |
|  | Center | 7% | 18% | 44% | 31% |
|  | Left side | −9% | 39% | 16% | 54% |
| Foot side center | Right side (Sample point 3) | 16% | −11% | 85% | 11% |
|  | Center | 3% | 3% | 55% | 38% |
|  | Left side (Sample point 4) | −8% | 15% | 25% | 68% |
| Foot side | Right side | 6% | −23% | 101% | 16% |
|  | Center | −9% | −15% | 71% | 54% |
|  | Left side | −16% | −1% | 34% | 83% |

Figure 12:
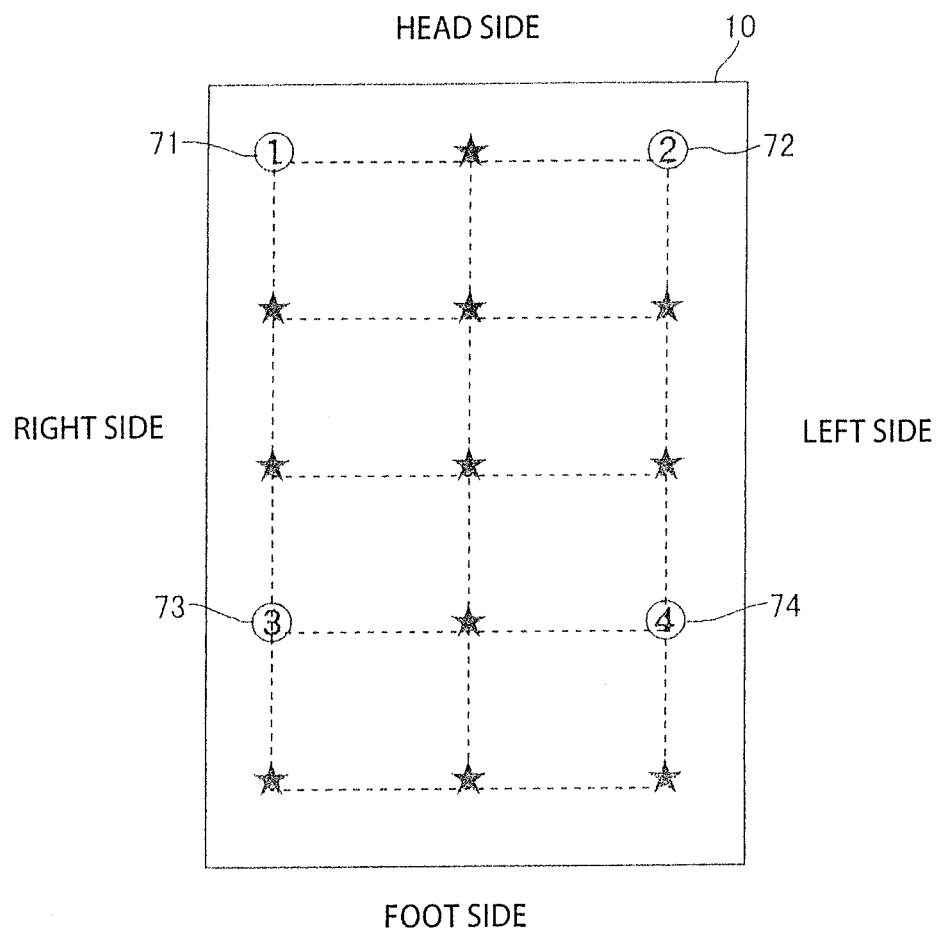
FIG. 12 is a plan view showing an example of sample points for a load table used in a center-of-gravity position detection process with respect to the watching system according to the first embodiment.

Table 1 shows the ratio of the load applied to the four pin sensors when load is applied at each sample point in FIG. 12.

Figure 13:
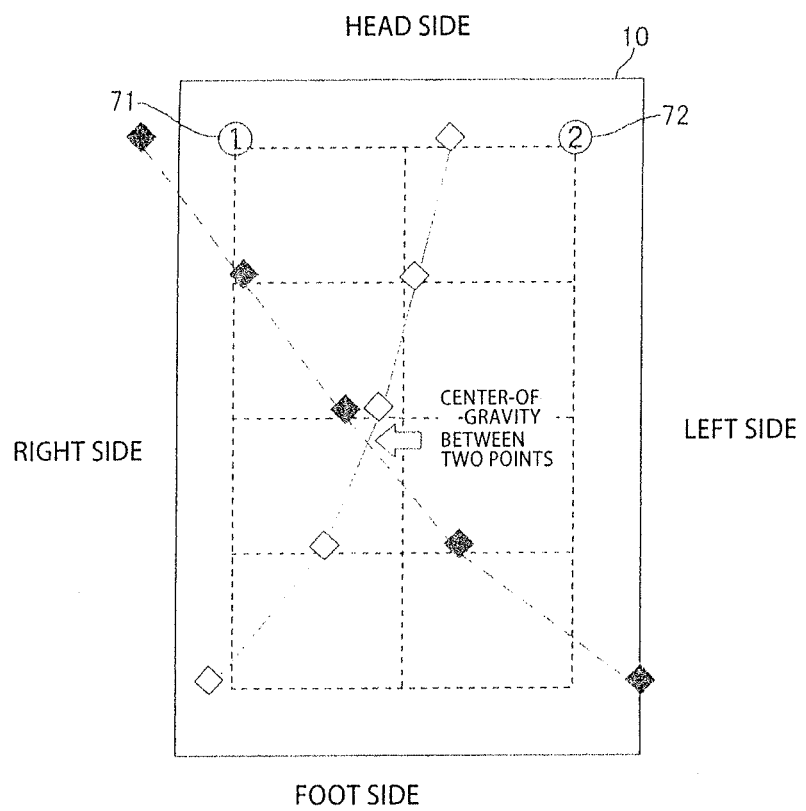
FIG. 13 is a plan view showing an example of detection of the center-of-gravity between two points with respect to the watching system according to the first embodiment.

1A) As shown in FIG. 13, the center-of-gravity position which may correspond to the right head load ratio with respect to the sum of the four points on the bed is calculated from the load table by linear interpolation. In FIG. 13, as an example, positions where the right head load ratio is 10% are shown using linear interpolation.

1B) The center-of-gravity position which may correspond to the left head load ratio with respect to the sum of the four points on the bed is calculated from the load table by linear interpolation. In FIG. 13, as an example, positions where the left head load ratio is 10% are shown using linear interpolation.

1C) An intersection point of a linear interpolation line with the right head load ratio of 10% and a linear interpolation line with the left head load ratio of 10% is calculated. The intersection point is the center-of-gravity position between the two points at the right head sensor 71 and the left head sensor 72 (see FIG. 13).

2) Next, the center-of-gravity position on the bed is detected from "center-of-gravity position with respect to the two points" in the four pin sensors 71 to 74. That is, the following four "center-of-gravity positions with respect to the two points" are detected in the process of Two points at a right head sensor 71 and a left head sensor 72

Two points at the right head sensor 71 and a right foot sensor 73

Two points at the left head sensor 72 and a left foot sensor 74

Two points at the right foot sensor 73 and the left foot sensor 74

Figure 14:
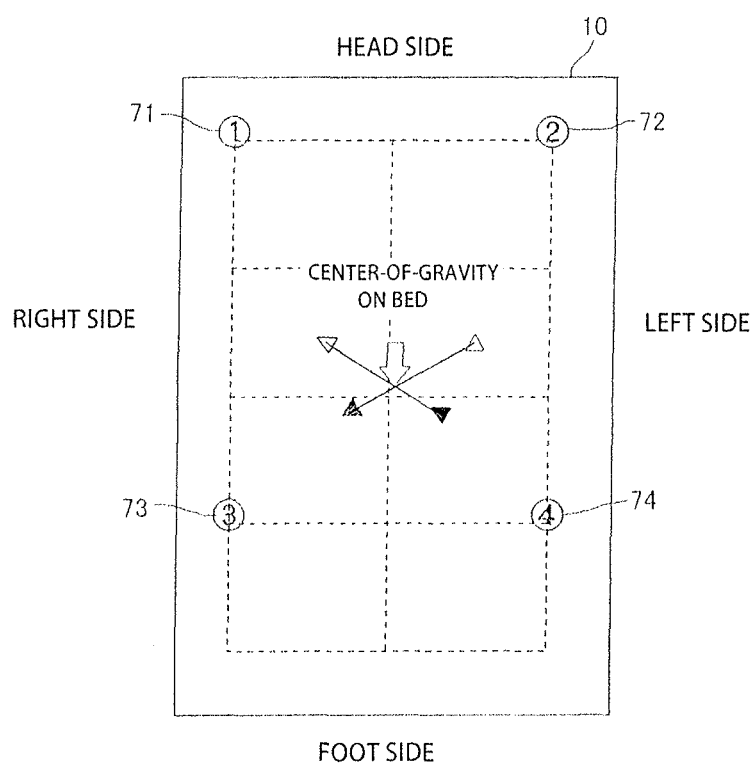
FIG. 14 is a plan view showing an example of detecting the center-of-gravity position on the bed from the center-of-gravity between two points with respect to the watching system according to the first embodiment.

Therefore, as illustrated in FIG. 14, the center-of-gravity position on the bed is detected from the intersection of these four "center-of-gravity positions with respect to the two points".

The outputs of the load/center-of-gravity detection unit 114 and the biological signal detection unit 110 are input to a bed-departure/bed-presence detection unit 116 including a bed-presence detection unit 116A, a sit-up detection unit 116B, and a bed-departure detection unit 116C, and the bed-departure/bed-presence is detected.

The output of the bed-departure/bed-presence detection unit 116 is input to a communication unit 118, then input to the display unit 120 including a load display unit 120A, a center-of-gravity display unit 120B, a respiratory rate display unit 120C, and a heartbeat rate display unit 120D, and displayed.

Next, referring to FIG. 15, a watching system to which a monitor camera is further added according to a second example will be described.

Figure 15:
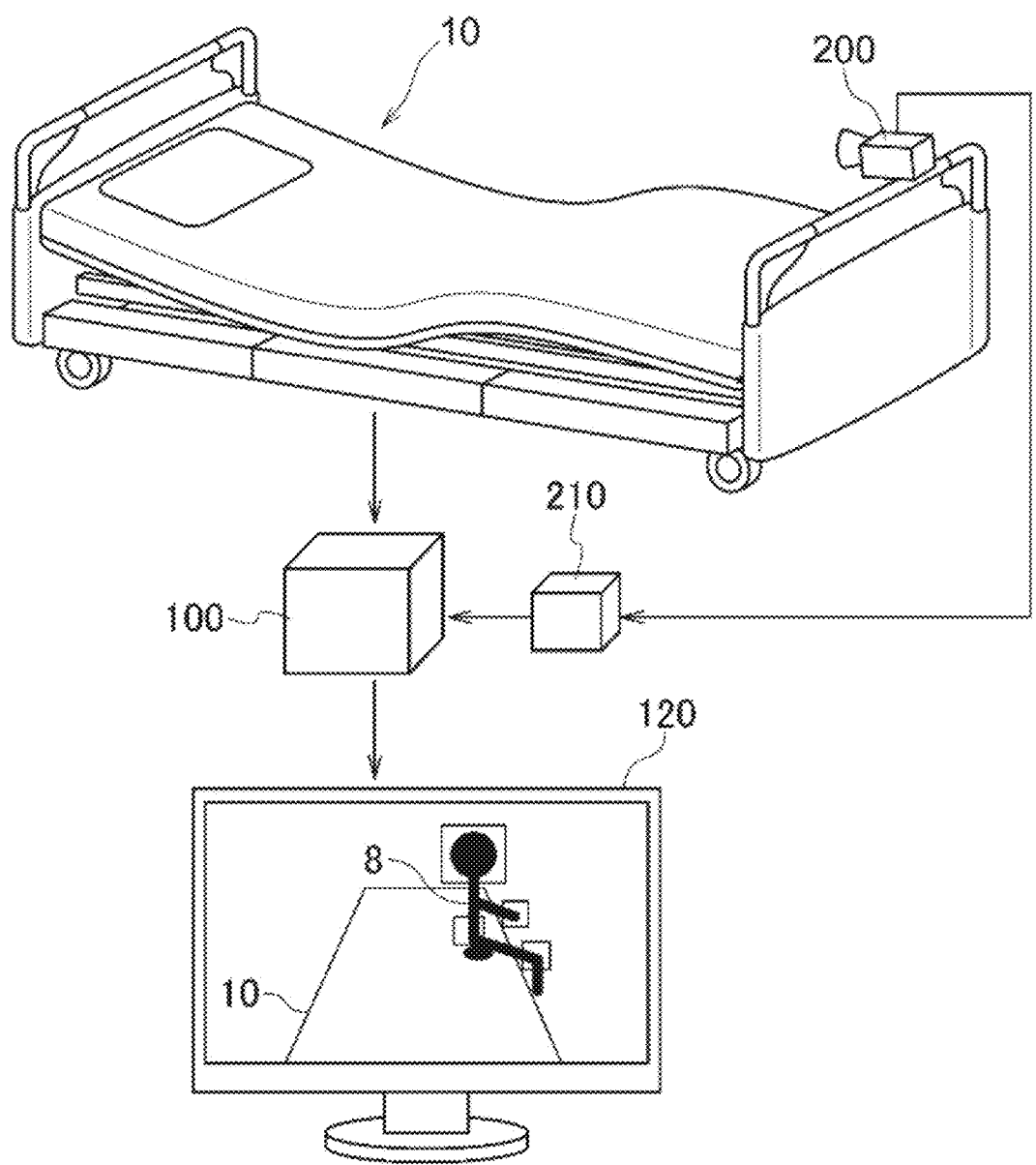
FIG. 15 is a block diagram showing the entire configuration of a watching system to which a camera is added according to the second example.

In this second example, as shown in FIG. 15, in addition to the watching system which is similar to that of the first example in FIG. 7, a monitor camera 200 provided on a footboard of the motorized bed 10, for example, and having a field of view directed from the foot side to the head side, and an image recognition unit 210 for recognizing human body parts (the head 8A, the torso 8B, the hand 8C, the leg 8D, etc.) of a patient 8 as an object or parts are provided.

Note that the monitor camera 200 is not limited to being disposed on the footboard, and may be disposed at another position from which the entire bed can be viewed.

According to the second example, in addition to the center-of-gravity detection result according to the first example, the object or parts of the patient 8 are recognized from the image of the monitor camera 200, and more accurate watching can be performed according to the recognition result. That is, combination of a two-dimensional image obtained by the monitor camera 200 with bed information is capable of highly reliable decision.

Figure 16:
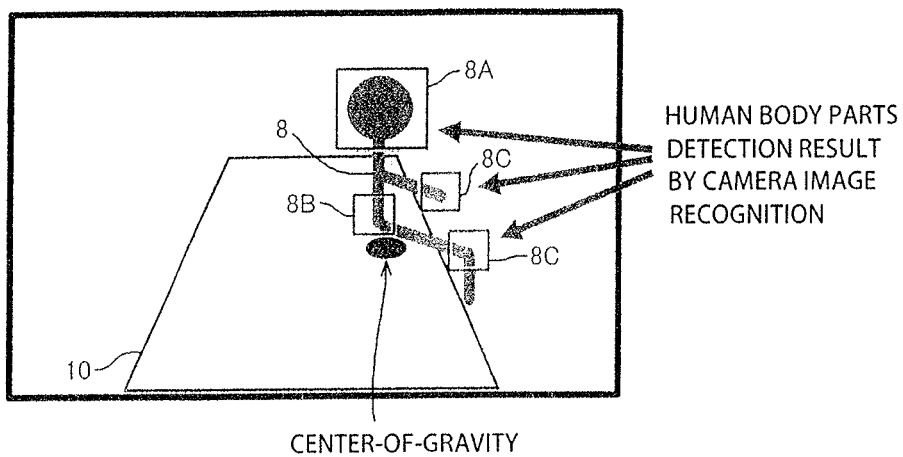
FIG. 16 is a diagram showing an example of a monitor screen according to a second example.

For example, as shown in FIG. 16, in a case where it is detected that the center-of-gravity is located at the end of the motorized bed 10 by the pin sensors 71 to 74, and furthermore, it is detected that the patient 8 is in the sitting position by the camera image recognition result, the watching is continued.

Figure 17:
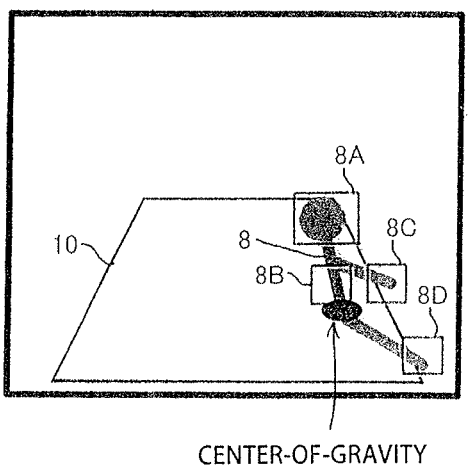
FIG. 17 is a diagram showing another example of the monitor screen according to the second example.

On the other hand, as shown in FIG. 17, when it is determined that the patient 8 is sleeping, it is decided that there is a risk of falling or the like, and so that necessary action can be taken such that an alarm is generated.

In this way, the combination of a two-dimensional image obtained by the monitor camera 200 with bed information is capable of highly reliable decision.

In addition, for example, video data can be recorded only when an event such as bed-departure, stumbling or falling occurs.

Furthermore, it is also possible to predict dangerous behavior by converting information on a living body, a load, a center-of-gravity, human behavior into data in real time and performing machine learning.

Note that the arrangement position and direction of the monitor camera 200 are not limited to the example in FIG. 15.

In the above-described embodiment, the present invention is applied to the motorized bed. However, the scope of the application of the present invention is not limited to this, and the present invention can be applied to a non-motorized nursing bed, a bed for medical care, a nursing care lifter, and further a bed for able-bodied people.

The pin sensor is not limited to being attached to the existing bed. It can be originally attached to the new bed.

The relations of the frames are not limited to the upper and lower position.

What is claimed is:

1. A load measuring pin sensor disposed as a connecting pin in a connecting portion of a plurality of frames of a bed, the load measuring pin sensor comprising:
 a shaft portion constituting the connecting pin;
 a force point portion provided on the shaft portion, a load from a first frame of the plurality of frames acting on the force point portion;
 a fulcrum portion provided at a position different from a position of the force point portion of the shaft portion, a stress from a second frame of the plurality of frames acting on the fulcrum portion;
 a sensing portion provided at a portion connecting the force point portion and the fulcrum portion of the shaft portion; and
 a strain gauge that detects strain occurring in the sensing portion,
 wherein one of the force point portion and the fulcrum portion has a cross section larger than a cross section of the shaft portion, the cross section of the one of the force point portion or the fulcrum portion having a shape other than a circular shape, and a pin sensor receiving portion on a frame side corresponding to the cross section of the one of the force point portion or the fulcrum portion is shaped to correspond to the shape other than the circular shape so that the load measuring pin sensor does not rotate, and wherein the other of the force point portion and the fulcrum portion has a portion having a rounded surface, the rounded surface being in contact with the plurality of frames.

2. The load measuring pin sensor according to claim 1, wherein the cross section of the one of the force point portion and the fulcrum portion is a cross section of a fulcrum portion located at a longitudinal center of the shaft portion.

3. The load measuring pin sensor according to claim 1, wherein the shape other than the circular shape is a quadrangle.

4. The load measuring pin sensor according to claim 1, wherein the sensing portion has a prismatic shape having a rectangular cross section.

5. A watching system comprising:
a watching bed including the load measuring pin sensor according to claim 1;
a signal processing unit that processes an output of the load measuring pin sensor to obtain a biological signal; and
a display unit that displays a processing result of the signal processing unit.

6. The watching system according to claim 5, further comprising a camera that monitors a measurement object on a bed.

7. A watching bed comprising:
a plurality of frames; and
a load measuring pin sensor disposed as a connecting pin in a connecting portion of the plurality of frames, the load measuring pin sensor comprising:
a shaft portion constituting the connecting pin;
a force point portion provided on the shaft portion, a load from a first frame of the plurality of frames acting on the force point portion;
a fulcrum portion provided at a position different from a position of the force point portion of the shaft portion, a stress from a second frame of the plurality of frames acting on the fulcrum portion;
a sensing portion provided at a portion connecting the force point portion and the fulcrum portion of the shaft portion; and
a strain gauge that detects strain occurring in the sensing portion,
wherein one of the force point portion and the fulcrum portion has a cross section larger than a cross section of the shaft portion, the cross section of the one of the force point portion or the fulcrum portion having a shape other than a circular shape, and a pin sensor receiving portion on a frame side corresponding to the cross section of the one of the force point portion or the fulcrum portion is shaped to correspond to the shape other than the circular shape so that the load measuring pin sensor does not rotate, and
wherein the other of the force point portion and the fulcrum portion has a portion having a rounded surface, the rounded surface being in contact with the plurality of frames.

* * * * *